United States Patent [19]

Nakanishi et al.

[11] Patent Number: 5,750,650
[45] Date of Patent: May 12, 1998

[54] FIBRINOLYTIC PROTEIN AND PRODUCTION METHOD THEREOF

[76] Inventors: Koichiro Nakanishi, 19-20, Karibadai 2-chome, Nishi-ku, Kobe, Hyogo 673; Keiichi Nomura, 18-6, Toyoura-cho, Higashiosaka, Osaka 579; Kyoko Tajima, Parumezon-Imadera 307, 4-1, Imadera, Nishi-ku, Kobe, Hyogo 673; Hajime Hiratani, 705-3, Tottori, Hannan-cho, Sennan-gun, Osaka 599-02; Kazuo Kato, Howaito Rejidensu 202, 8-15, Minamigoyo 3-chome, Kita-ku, Kobe, Hyogo 651-11, all of Japan

[21] Appl. No.: 67,180

[22] Filed: May 24, 1993

Related U.S. Application Data

[63] Continuation-in-part of Ser. No. 618,494, Nov. 27, 1990, abandoned.

[30] Foreign Application Priority Data

Nov. 27, 1989 [JP] Japan ................. 1-308191

[51] Int. Cl.$^6$ ................. C07K 14/32; C07K 1/20
[52] U.S. Cl. ................. 530/350; 530/416; 530/417; 435/212; 435/217; 435/222; 424/94.1; 424/94.3; 424/94.64
[58] Field of Search ................. 530/350, 416, 530/417; 435/212, 217, 222; 424/94.1, 94.3, 94.64

[56] References Cited

U.S. PATENT DOCUMENTS

| | | | |
|---|---|---|---|
| 4,110,477 | 8/1978 | Naruse et al. | 426/46 |
| 5,260,206 | 11/1993 | Aretz et al. | 435/195 |

OTHER PUBLICATIONS

Abstracts of Hiratani et al., Jap Pat No. J01180834, dated Jul., 1989, from Databases 'World Pat Index' and 'JAP10'.

Abstracts of Morimoto N (assignee), JAP Pat No. J 6 1162184, dated Jun., 1986, from Databases 'World Pat Index' and 'JAP10'.

Sumi et al., Amino Acid Sequence from Database 'PIR', for Fibrinolysis Enzyme Natto Kinase, Accession #JS0517, dated Mar. 1992.

Sumi, H, Amino Acid Seq. from Database 'PIR' for Fibrinolysis Enzyme Natto Kinase, Accession #JS0601 dated Dec. 1991.

Kurihara et al., Amino Acid Sequence form Database 'PIR', for *Bacillus Subtilis*, (Amylosachariticus), Accession #A00971, dated Dec. 1986.

Harris, E. L. V. et al, "Protein purification and methods", IRL Press, 1989, pp. 51–66, 221–230.

Chem. Abstracts, vol. 112, 1990, 132477b, Hiratani et al, effective date 18 Jul. 1989.

Chem. Abstracts, vol. 103, 1985, 173826x, Sumi et al.

Hames, in Gel Electrophoresis of Proteins, Chap. 1, IRL Press, Eds. Hames et al, 1981.

*Primary Examiner*—Chhaya D. Sayala
*Attorney, Agent, or Firm*—Burgess, Ryan and Wayne

[57] ABSTRACT

A novel peptide having molecular weight of 31,000 (SDS-PAGE) is obtained from aqueous extract of Natto or the culture of *Bacillus natto* by purification procedures including alcohol fractionation and/or salting out and hydrophobic chromatography, and the physicochemical properties, including the amino acid sequence, of the peptide are determined.

The peptide is active in fibrinolysis, exhibits strong thrombolytic activity by oral administration and is useful as an oral thrombolytic agent.

4 Claims, 1 Drawing Sheet

FIBRINOLYTIC PROTEIN AND PRODUCTION METHOD THEREOF

This application is a continuation-in-part of application Ser. No. 07/618,494, filed Nov. 27, 1990 now abandoned.

BACKGROUND OF THE INVENTION

1. Field of the Invention

This invention relates to a protein in high purity, having fibrinolytic activity even when administered orally and a production method thereof.

2. Description of the Related Art

Thrombus has become a serious problem as a cause of various diseases such as peripheral arteriovenous thrombosis, pulmonary embolism, myocardial infarction, cardiac infarction, cerebral infarction, retinal arteriovenous thrombosis, or many other diseases. Sumi et al. have filed a patent application for a method of obtaining a fibrinolytic enzyme produced by *Bacillus natto* (Patent Application Kokai No. 162184/1986). Furthermore, Hiratani et al., filed another application (Patent Application Kokai No. 180834/1989) about a thrombolytic agent for oral administration comprising the above enzyme, whereby the efficacy of the enzyme was clarified. According to these applications, the above enzyme is white powder having molecular weight of about 20,000.

However, the purity of the fibrinolytic enzyme in these publications was low and hence its essential feature could not be clarified and a large amount, such as 1 g per adult dog, of administration was required to demonstrate the activity.

The present inventors have succeeded to obtain substantially pure fibrinolytic protein from Natto (a Japanese food prepared by fermenting steamed soybeans in straw) or the culture of *Bacillus natto*.

SUMMARY OF THE INVENTION

The protein of this invention is contained in Natto, *Bacillus natto* or the culture of *Bacillus natto*, therefore, the protein can be obtained by extracting these materials with an aqueous solvent such as water or aqueous solution of salt(s), and then purifying the aqueous extract with a combination of at least two of fractionation means, for example, fractionation with alcohol, salting out with ammonium sulfate, hydrophobic chromatography employing a carrier such as Butyl-Sepharose® (produced by Pharmacia Co.) etc., anion exchange chromatography employing a carrier such as Mono-Q or S-Sepharose® (produced by Pharmacia Co.), gel-filtration chromatography employing Sephacryl® S-200 (produced by Pharmacia Co.), etc. In order to obtain the enzyme in high purity, particularly effective is hydrophobic chromatography.

DESCRIPTION OF THE PREFERRED EMBODIMENTS

The present inventors conducted research into the highly purified protein thus obtained, and as the results, succeeded to clarify its whole physico-chemical properties. Furthermore, it was found that this substance exhibits fibrinolytic activity even in a small dose of about 20 mg per adult dog, which lead to the establishment of this invention.

This invention is directed to a protein which comprises the polypeptide having the amino acid sequence represented by the formula (SEQ ID NO:1:),

```
Ala Gln Ser Val Pro Tyr Gly Ile Ser Gln Ile Lys Ala Pro Ala
 1               5                  10                 15
Leu His Ser Gln Gly Tyr Thr Gly Ser Asn Val Lys Val Ala Val
                20                  25                 30
Ile Asp Ser Gly Ile Asp Ser Ser His Pro Asp Leu Asn Val Arg
                35                  40                 45
Gly Gly Ala Ser Phe Val Pro Ser Glu Thr Asn Pro Tyr Gly Asp
                50                  55                 60
Gly Ser Ser His Gly Thr His Val Ala Gly Thr Ile Ala Ala Leu
                65                  70                 75
Asn Asn Ser Ile Gly Val Leu Gly Val Ala Pro Ser Ala Ser Leu
                80                  85                 90
Tyr Ala Val Lys Val Leu Asp Ser Thr Gly Ser Gly Gln Tyr Ser
                95                 100                105
Trp Ile Ile Asn Gly Ile Glu Trp Ala Ile Ser Asn Asn Met Asp
               110                 115                120
Val Ile Asn Met Ser Leu Gly Gly Pro Thr Gly Ser Thr Ala Leu
               125                 130                135
Lys Thr Val Val Asp Lys Ala Val Ser Ser Gly Ile Val Val Ala
               140                 145                150
Ala Ala Ala Gly Asn Glu Gly Ser Ser Gly Ser Thr Ser Thr Val
               155                 160                165
Gly Tyr Pro Ala Lys Tyr Pro Ser Thr Ile Ala Val Gly Ala Val
               170                 175                180
Asn Ser Ser Asn Gly Arg Ala Ser Phe Ser Ser Val Gly Ser Glu
               185                 190                195
Leu Asp Val Met Ala Pro Gly Val Ser Ile Gln Ser Thr Leu Pro
               200                 205                210
Gly Gly Thr Tyr Gly Ala Tyr Asn Gly Thr Ser Met Ala Thr Pro
               215                 220                225
His Val Ala Gly Ala Ala Ala Leu Ile Leu Ser Lys His Pro Thr
               230                 235                240
Trp Thr Asn Ala Gln Val Arg Asp Arg Leu Glu Ser Thr Ala Thr
               245                 250                255
Tyr Leu Gly Asn Ser Phe Tyr Tyr Gly Lys Gly Leu Ile Asn Val
               260                 265                270
Gln Ala Ala Ala Gln
               275
``` and having the following specific properties:
(a) Molecular weight: 31,000 (SDS-PAGE),
(b) Isoelectric point: 8.5–8.9,
(c) Fibrinolitic activity, and
(e) Hydrolytic activity to the synthetic substrate of Suc-Ala-Ala-Pro-Phe-MCA 4-methylcoumarine amide, (SEQ ID NO:2) and a method for producing a fibrinolytic protein characterized by subjecting the aqueous extract of Natto or the culture of *Bacillus natto* to fractionation with alcohol and/or salting out, purifying the resulting insoluble material by chromatography including at least hydrophobic chromatography, and recovering a fraction containing the protein as described above.

The protein of this invention can be advantageously extracted from Natto or the culture of *Bacillus natto*.

The aqueous extract of Natto or the culture of *Bacillus natto* can be obtained by extracting the material with water or neutral or weakly basic aqueous solution of salt(s). The liquid portion of a culture obtained by cultivating *Bacillus natto* in an aqueous medium may be employed as the aqueous extract.

The aqueous solution of salt(s) employed in the extraction includes, for example, a phosphate buffer (pH 6–8) containing a salt such as 0.01M–0.3M of sodium chloride or potassium chloride, or 0.005M–0.1M tris(hydroxymethyl) aminomethane (herein after abbreviated as "tris") buffer (pH 7–9) containing 0.01M–0.3M of sodium chloride or potassium chloride.

There may be obtained a crude precipitate fraction by adding an organic solvent or a salt to the above crude extract. For example, the crude precipitate fraction can be obtained by adding to the aqueous extract an alcohol such as ethanol or methanol so as to make its concentration 60%–80% (v/v), preferably 75%, or ammonium sulfate so as to make its concentration 40–60% (w/v), preferably 50% (w/v).

The fraction of crude precipitates can be further purified by carrying out chromatography mentioned below;

The crude fraction is adsorbed on a carrier such as Butyl Sepharose® or Alkyl Sepharose® (produced by Pharmacia Co.), etc. which has hydrophobic groups and has been equilibrated with a neutral or weakly basic buffer containing sodium sulfate, and then eluted from the carrier with water or neutral or weakly basic buffer, whereby the fraction can be extracted and purified.

For example, as the solvent in the adsorption step, there may by employed a phosphate buffer (pH 6–8) containing 1.3–3M of sodium sulfate or a tris-buffer (pH 7–8) containing the same amount of sodium sulfate as above.

As a different method for purification, co-existing impurities in the crude fraction can be removed by adsorbing the fraction on an anion exchanger equilibrated with a neutral or weakly basic buffer.

As the anion exchanger, there may be employed, for example, Mono-Q-Sepharose® (wherein particle distribution is extremely narrow, produced by Pharmacia Co.) or Q-Sepharose® Fast Flow (wherein the cross-linking ratio of Sepharose is increased to fortify the material physically and chemically, produced by Pharmacia Co.).

Furthermore, it can be purified by allowing it to be adsorbed on a cation exchanger equilibrated with a neutral or weakly basic buffer solution and then to elute with a neutral or weakly basic buffer solution containing salt(s).

As the carrier for the adsorption, there may be employed a cation exchanger such as S-Sepharose® First-Flow (produced by Pharmacia Co.) equilibrated with a buffer such as 0.005M–0.05M phosphate buffer solution (pH 6–8) etc.

The elution from the carrier may be carried out by employing a buffer solution such as 0.005M to 0.05M phosphate buffer (pH 6–8) containing 0.2 to 1M, preferably 0.4 to 0.6M of sodium chloride, or 0.005M to 0.05M tris-buffer (pH 7–9) etc.

Furthermore, the enzyme of present invention may be purified by applying on a gel filtration carrier equilibrated with a neutral or weakly basic buffer solution. As the gel filtration carrier, there may be employed Sephacryl S-200 or Sephadex G-75 etc. For the equilibration of the carrier, there may be employed a buffer solution such as 0.005M to 0.05M phosphate buffer solution (pH 6–8) containing 0.05 to 0.5M, preferably 0.2M, sodium chloride or 0.005M to 0.05M tris-buffer solution (pH 7–9) etc.

Accordingly, in one embodiment, the production method for preparing the fibrinolytic protein can be conducted in a sequence of steps comprising:

1) adding an alcohol or ammonium sulfate to an aqueous extract of Natto or *Bacillus natto* to precipitate a crude fraction, 2) applying the crude fraction on a hydrophobic carrier equilibrated with a neutral or weakly basic buffer to adsorb the fraction onto the column and eluting an adsorbed fraction with water or neutral or weakly basic buffer from the column.

3) passing the eluate through an anion exchanger equilibrated with a neutral or weakly basic buffer to adsorb the impurities onto the exchanger and obtaining a purified fraction as the effluent, or applying the eluate on a cation exchanger equilibrated with a neutral or weakly basic buffer to adsorb the fraction onto the exchanger and eluting a purified fraction with a neutral or weakly basic buffer containing a salt, 4) applying the purified fraction on a gel filtration carrier equilibrated with a neutral or weakly basic buffer containing a salt, and 5) recovering a purified fibrinolytic protein.

The present fibrinolytic active protein can be obtained in high yield by employing these chromatographies in a combination of at least two of them.

The protein thus obtained can dissolve thrombus or prevent the formation of thrombus by oral administration in an amount of 20 to 500 mg, preferably 50 to 300 mg at a time or lesser amounts to several times daily to an adult.

As mentioned above, the present invention provides a harmless and highly pure protein exhibiting fibrinolytic activity by oral administration in a small amount, which is usable as a fibrinolytic agent for oral administration.

In the following, the present protein is described in detail:

The protein of the present invention comprises the structure of a peptide having the amino acid sequence represented by the formula (SEQ ID NO:1:),

```
Ala Gln Ser Val Pro Tyr Gly Ile Ser Gln Ile Lys Ala Pro Ala
 1               5                  10                   15
Leu His Ser Gln Gly Tyr Thr Gly Ser Asn Val Lys Val Ala Val
                20                  25                   30
Ile Asp Ser Gly Ile Asp Ser Ser His Pro Asp Leu Asn Val Arg
                35                  40                   45
Gly Gly Ala Ser Phe Val Pro Ser Glu Thr Asn Pro Tyr Gly Asp
                50                  55                   60
Gly Ser Ser His Gly Thr His Val Ala Gly Thr Ile Ala Ala Leu
                65                  70                   75
Asn Asn Ser Ile Gly Val Leu Gly Val Ala Pro Ser Ala Ser Leu
                80                  85                   90
Tyr Ala Val Lys Val Leu Asp Ser Thr Gly Ser Gly Gln Tyr Ser
                95                  100                  105
Trp Ile Ile Asn Gly Ile Glu Trp Ala Ile Ser Asn Asn Met Asp
                110                 115                  120
Val Ile Asn Met Ser Leu Gly Gly Pro Thr Gly Ser Thr Ala Leu
                125                 130                  135
Lys Thr Val Val Asp Lys Ala Val Ser Ser Gly Ile Val Val Ala
                140                 145                  150
Ala Ala Ala Gly Asn Glu Gly Ser Ser Gly Ser Thr Ser Thr Val
                155                 160                  165
Gly Tyr Pro Ala Lys Tyr Pro Ser Thr Ile Ala Val Gly Ala Val
                170                 175                  180
Asn Ser Ser Asn Gly Arg Ala Ser Phe Ser Ser Val Gly Ser Glu
                185                 190                  195
Leu Asp Val Met Ala Pro Gly Val Ser Ile Gln Ser Thr Leu Pro
                200                 205                  210
Gly Gly Thr Tyr Gly Ala Tyr Asn Gly Thr Ser Met Ala Thr Pro
                215                 220                  225
His Val Ala Gly Ala Ala Ala Leu Ile Leu Ser Lys His Pro Thr
                230                 235                  240
Trp Thr Asn Ala Gln Val Arg Asp Arg Leu Glu Ser Thr Ala Thr
                245                 250                  255
Tyr Leu Gly Asn Ser Phe Tyr Tyr Gly Lys Gly Leu Ile Asn Val
                260                 265                  270
Gln Ala Ala Ala Gln,
                275
``` and has the following specific properties;
(a) Molecular weight: 31,000 (SDS-PAGE),
(b) Isoelectric pH: 8.5–8.9,
(c) Fibrinolitic activity, and
(e) Hydrolytic activity to a synthetic substrate.

The respective properties mentioned above were determined by the methods described in the following Experiment a) to d).

Figure 1:
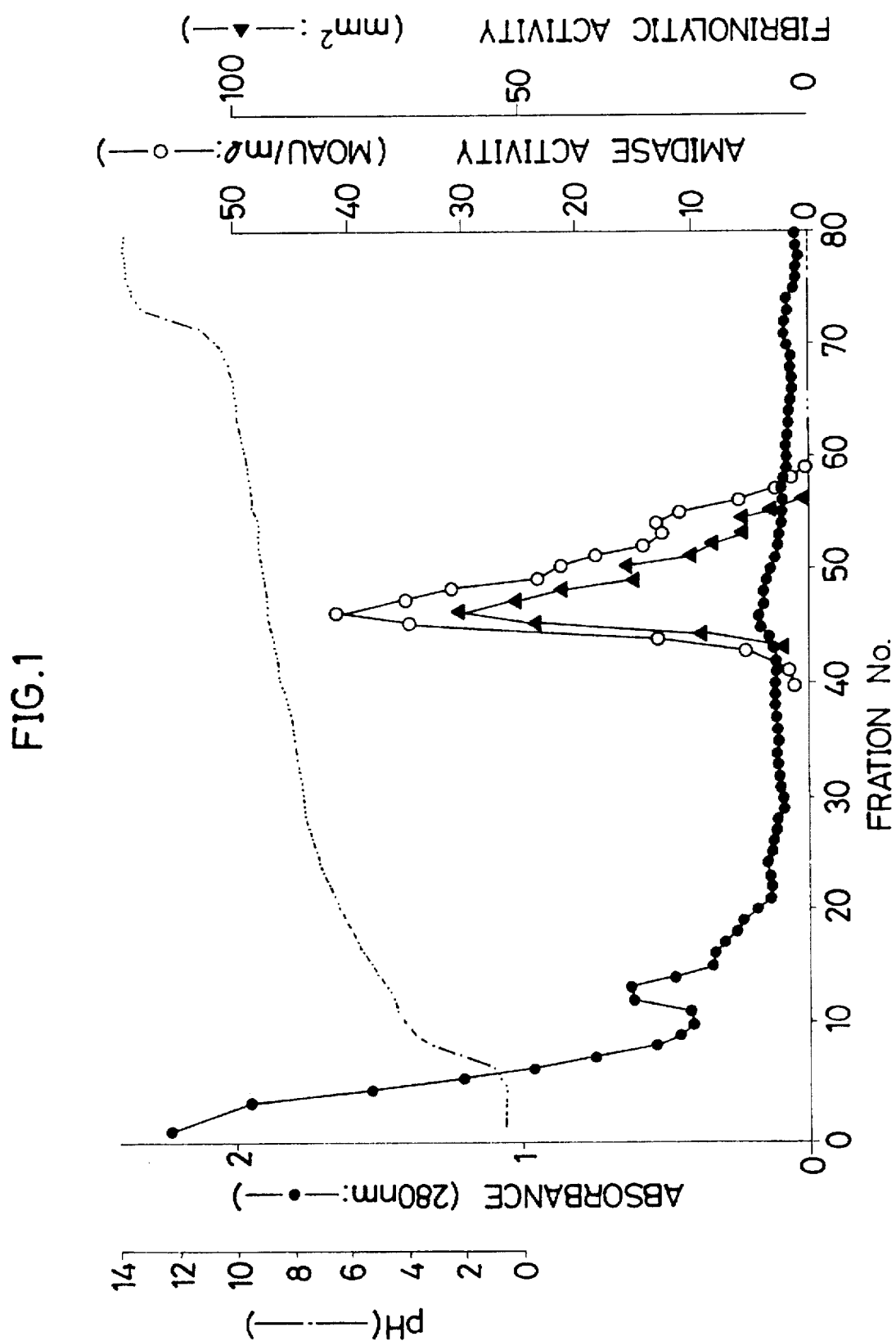
FIGURE 1 shows the result obtained by the isoelectric fractionation of present protein in Experiment b).

EXPERIMENT a) Method of Determining Molecular Weight:

To a sample of protein prepared by the method described in Example 1, SDS (sodium dodecyl sulfate) and betermercaptoethanol were added and the mixture was boiled at 100° C. for 3 minutes.

The sample thus reacted with SDS was subjected to SDS-electrophoresis (SDS-PAGE), making use of an electrophoresis apparatus (Phast System® produced by Pharmacia Co.), employing 12.5% acrylamide gel (Phast Gel Homogeneous®, produced by Pharmacia Co.) and SDS buffer strip.

Staining was carried out by employing a silver stain kit (Silver Stain Kanto®, produced by Kanto Chemical Co.). Making use of a kit of determining molecular weight by electrophoresis (HMW kit E (for low molecular weight)), calibration curve was prepared and the molecular weight of the protein was determined.

The protein of present invention exhibited single stain band at molecular weight 31,000.

b) Method of Determining Isoelectric Point:

A sugar density gradient wherein density inclines larger from upper layer to lower layer of a column was prepared by piling up Ampholine® (pH 3.5–10.0; produced by Pharmacia Co.) on a solution of sugar in Ampholine® (pH 7.0–9.0), employing isoelectric focusing electrophoresis apparatus (110 ml, produced by Kato Seisakusho). On this procedure, the protein prepared by the method of Example 1 was piled at the center of the column. A pH gradient was prepared by charging electricity to the column at 500 V for 43 hours.

By taking out solution in order from the bottom layer, there were obtained 80 fractions each having gradually increased pH. The amount of protein (absorbance at 280 nm) and pH as well as fibrinolytic activity and amidase activity of each fraction were determined.

The results are shown in FIGURE 1. The isoelectric point of the protein of present invention was 8.5–8.9.

c) Evaluation of Activity with Fibrin Plate (Fibrinolytic Activity):

Fibrin standard plate (T. Astrup and S. Mullertz, Archs. Biochem. Biophys., 40, 346–351, 1952) was prepared and 10 μl of the protein prepared by the method of Example 1 was spotted on the plate. After maintained the plate at 37° C. for 18 hours, the dissolved area (mm$^2$) of each fibrin film was measured. The dissolved area of fibrin with 4-fold dilution of the protein was 240.3 mm$^2$/ml.

d) Evaluation of Amidase Activity by Employing Suc-Ala-Ala-Pro-Phe-MCA (SEQ ID NO:2:) substrate:

The amidase activity of the protein prepared by the method of Example 1 was determined employing Suc-Ala-Ala-Pro-Phe-MCA (SEQ ID NO.2) produced by Peptide Kenkyusho.

After dissolving Suc-Ala-Ala-Pro-Phe-MCA (SEQ ID NO:2) in dimethylsufoxide (DMSO), the solution was added to 0.05M tris-HCl buffer solution (pH 8.0) containing 0.15M of sodium chloride to make 10 mM solution of the substrate. The protein was suitably diluted with 0.05M tris-HCl buffer solution (pH 8.0) containing 0.15M of sodium chloride to make sample solutions. To 1 ml of the substrate solution being maintained at 37° C., 0.1 ml of the sample solution was added and allowed to react at 37° C. for 30 minutes. The reaction was stopped by adding 4 ml of 17% acetic acid thereto. Employing a fluorophotometer produced by Shimadzu Corp., the amount of 4-methylcoumarin (MCA) formed by the hydrolysis of Suc-Ala-Ala-Pro-Phe-MCA (SEQ ID NO:2) was calculated by comparing the strength of 460 nm fluorescence emitted from the sample under exciting by 380 nm light with that from a known amount of AMC. One unit of amidase activity (1 MCAU) was represented by the amount of enzyme which produces 1 nM of AMC per minute by hydrolizing Suc-Ala-Ala-Pro-Phe-MCA. (SEQ ID NO:2:).

The substrate-hydrolyzing activity of the protein obtained by the method of Example 1 was 107.6 MCAU/ml.

e) Amino Acid Composition:

Each 220 pM of the protein obtained by the method of Example 1 was hydrolyzed in a sealed vacuum tube with 6N hydrochloric acid containing 1 % of phenol at 110° C. for 24, 48 or 72 hours, respectively, and then, employing an amino acid analyzer (Model 6300, produced by Beckmann Co.), the amino acid composition of each hydrolyzed protein was analyzed. Provided that values at 0 hour were extrapolated regarding serine and threonine, and values at 72 hours were employed regarding valine, isoleucine and leucine. Furthermore, regarding tryptophan, its value was obtained by hydrolyzing with 3N mercaptoethanesulfonic acid. Amino acid analysis after oxidation with performic acid revealed that the protein contains no cystine (and cysteine). The amino acid composition of the protein in pure state and amino acid sequence described below in Example 1 could not be revealed until obtaining the protein in high purity by the method developed under intensive research in the course of establishing present invention.

Table 1 shows the result of the amino acid analysis, wherein it is cleared that the protein exhibits high homology with some enzymes of subtilisin family, particularly subtilisin amylosacchariticus.

TABLE 1

| Amino acid | Amino acid composition of the protein of present invention | | | |
|---|---|---|---|---|
| | Present protein | Subtilisin | | |
| | | Carsberg | BPN' | Amilosacchariticus |
| Asx | 25 | 28 | 28 | 25 |
| Thr | 19 | 19 | 13 | 17 |
| Ser | 39 | 32 | 37 | 41 |
| Glx | 15 | 12 | 15 | 15 |
| Pro | 13 | 9 | 14 | 13 |
| Gly | 33 | 35 | 33 | 33 |
| Ala | 34 | 41 | 37 | 35 |
| Val | 28 | 31 | 30 | 25 |
| Met | 4 | 5 | 5 | 4 |
| Ile | 16 | 10 | 13 | 16 |
| Leu | 15 | 18 | 15 | 15 |
| Tyr | 12 | 13 | 10 | 12 |
| Phe | 3 | 4 | 3 | 3 |
| Lys | 8 | 9 | 11 | 8 |
| His | 6 | 5 | 6 | 6 |
| Arg | 4 | 4 | 2 | 4 |
| Cys | 0 | 0 | 0 | 0 |
| Trp | 3 | 1 | 3 | 3 |
| Total | 275 | 274 | 275 | 275 |

Present invention is described more concretely by the examples referred below:

EXAMPLE 1

By extracting 20 kg of Natto obtained from the market with 35 L of physiological saline, crude extract containing 1.8 MCAU/mg of protein was obtained. Ethanol was added to the extract to make 50 % ethanol solution which was then centrifuged, and, to the supernatant, further ethanol was added to precipitate 936 g of a fraction with 75% ethanol. This precipitate fraction was dissolved in 0.01M PB (phosphate buffer solution, pH 7.0) containing 1.5M of ammonium sulfate, adsorbed on Butyl-Sepharose® (produced by Pharmacia Co.) equilibrated with the same buffer solution, eluted from the carrier with 0.01M PB (pH 7.0), and then salted out from the eluate by adding 50% w/v ammonium sulfate thereto to obtain 1085 g of a protein fraction (193 MCAU/mg). Purification efficiency in the above processes of treatment with Butyl-Sepahrose and subsequent salting out with ammonium sulfate was 20.3 times, and the rate of recovering activity by the end of the process was 42.5%.

The protein fraction was subjected to desalting and concentration, and passed through 1 ml column of anion exchanger, Mono-Q® (produced by Pharmacia Co.), equilibrated with tris-HCl (pH 7.0) to obtain 706 mg of a protein fraction (204 MCAU/mg). This fraction was subjected to the hydrophobic chromatography consisting of dissolving the fraction in 0.01M PB (pH 7.0) containing 1.5M of ammonium sulfate, adsorbing on 1 ml of Alkyl-Superose® (produced by Pharmacia Co.) equilibrated with the same PB, and eluting from the carrier with 0.01M PB (pH 7.0) to obtain 277 mg of protein (390 MCAU/mg). The recovery rate of activity of total processes was 22.0%. The properties and purity of this fraction are shown in the previous Experiment concerning properties.

The purified protein was digested to fragments with lysyl-endopeptidase and the fragments were purified by reverse HLPC to obtain 9 fractions. The amino acid sequence of each fraction was determined by applying the fraction to Model 477A/120A produced by Applied Biosystem Co. If necessary, each peptide fragment was further digested with chymotrypsin and purified, and then the sequence was determined.

The results are shown in Table 2. The mutating sites of present protein to subtilisin amilosacchariticus were 4 positions of $^{130}S \rightarrow ^{130}T$, $^{102}S \rightarrow ^{102}T$, $^{192}A \rightarrow ^{192}V$ and $^{259}D \rightarrow ^{259}N$.

TABLE 2

Total Amino acid sequence of present protein (SEQ ID NO:1:)

```
Ala Gln Ser Val Pro Tyr Gly Ile Ser Gln Ile Lys Ala Pro Ala
 1           5                  10                     15
Leu His Ser Gln Gly Tyr Thr Gly Ser Asn Val Lys Val Ala Val
            20                  25                     30
Ile Asp Ser Gly Ile Asp Ser Ser His Pro Asp Leu Asn Val Arg
            35                  40                     45
Gly Gly Ala Ser Phe Val Pro Ser Glu Thr Asn Pro Tyr Gly Asp
            50                  55                     60
Gly Ser Ser His Gly Thr His Val Ala Gly Thr Ile Ala Ala Leu
            65                  70                     75
Asn Asn Ser Ile Gly Val Leu Gly Val Ala Pro Ser Ala Ser Leu
            80                  85                     90
Tyr Ala Val Lys Val Leu Asp Ser Thr Gly Ser Gly Gln Tyr Ser
            95                 100                    105
Trp Ile Ile Asn Gly Ile Glu Trp Ala Ile Ser Asn Asn Met Asp
           110                 115                    120
Val Ile Asn Met Ser Leu Gly Gly Pro Thr Gly Ser Thr Ala Leu
           125                 130                    135
Lys Thr Val Val Asp Lys Ala Val Ser Ser Gly Ile Val Val Ala
           140                 145                    150
Ala Ala Ala Gly Asn Glu Gly Ser Ser Gly Ser Thr Ser Thr Val
           155                 160                    165
Gly Tyr Pro Ala Lys Tyr Pro Ser Thr Ile Ala Val Gly Ala Val
           170                 175                    180
Asn Ser Ser Asn Gly Arg Ala Ser Phe Ser Ser Val Gly Ser Glu
           185                 190                    195
Leu Asp Val Met Ala Pro Gly Val Ser Ile Gln Ser Thr Leu Pro
           200                 205                    210
Gly Gly Thr Tyr Gly Ala Tyr Asn Gly Thr Ser Met Ala Thr Pro
           215                 220                    225
His Val Ala Gly Ala Ala Ala Leu Ile Leu Ser Lys His Pro Thr
           230                 235                    240
Trp Thr Asn Ala Gln Val Arg Asp Arg Leu Glu Ser Thr Ala Thr
           245                 250                    255
Tyr Leu Gly Asn Ser Phe Tyr Tyr Gly Lys Gly Leu Ile Asn Val
           260                 265                    270
Gln Ala Ala Ala Gln
           275
```

EXAMPLE 2

From 20 kg of Natto, 630 mg of crude protein was obtained in the same manner as in Example 1 with elution from Butyl-Sepharose and purified by the following procedures;

The crude protein was adsorbed on S-Sepharose Fast Flow® (produced by Pharmacia Co.) equilibrated with 0.05M phosphate buffer solution (pH 7.0), eluted from the carrier with 0.05M phosphate buffer solution (pH 7.0) containing 0.5M of sodium chloride and further purified employing Sephacryl® S-200 (produced by Pharmacia Co.) equilibrated with 10 mM phosphate buffer solution containing 0.2M of sodium chloride to obtain 257 mg of purified protein fraction (379 MCAU/mg). Recovering rate of activity through total processes was 18.0%.

EXAMPLE 3

A culture of *Bacillus natto* (100 ml) which has been pre-cultured in nutrient agar medium was inoculated in 10,000 ml of Henneberg's liquid and cultured at 43° to 45° C. for 45 hours. The liquid culture of *Bacillus natto* was then centrifuged at 1,850×g for 10 minutes, and the resulting supernatant was subjected to salting out by adding 50% (w/v) of ammonium sulfate thereto to obtain 35 g of crude product.

The crude product was purified by the processes of 10 treatment with Butyl-Sepharose, Mono-Q and alkyl-Superose in order according to Example 1 to obtain 53 mg of purified protein fraction (310 MCAU/mg protein). Total recovering rate of activity was 18.9%.

EXAMPLE 4 (ACTIVITY)

In the lateral latent vein of mongrel adult dogs (male, 10–16 kg), artificial thrombi were prepared employing 0.4 mg of 5 % bovine fibrinogen and 50 units/ml of bovine thrombin by the method of Sasaki et al (K. Sasaki et al., Life Science, 27, 1659–1685, 1980). Four enteric capsules containing 10 mg/capsule of the protein produced by the method described in Example 1 were administered at one time to each dog. After the capsules moved to the duodenum, blood was collected from the dog and euroglobulin-dissolving time was measured by the above Sasaki et al's method as well as angiography by X ray was carried out after 4 ml of Angiografin® (produced by Schering, West Germany) was injected taking 2 seconds.

As the results, it was found that the contrast group (N=3) to which capsules not containing present protein were administered did not exhibit variation in ELT for 30 minutes to 12 hours and the dissolving of the artificial thrombus was not observed. To the contrary, in the group to which present protein was administered, ELT was 33±6 minutes (p<0.02) at 30 minutes after the administration, 42±10 minutes (p<0.09) after 1 hour, 52±8 minutes (p<0.5) after 3 hours and 53±8 minutes (p<0.5) after 6 hours, showing shortening (i.e. acceleration in fibrinolysis). Furthermore, it was confirmed that the artificial thrombi were completely dissolved within 5 hours of ELT in the group to which present protein was administered.

From the above facts, it is apparent that present protein exhibits fibrinolytic activity at an extremely small amount as compared with an effective dose, not less than 1 g, of known crude protein obtained from *Bacillus natto*.

---

We claim:

1. A method for producing a biologically pure fibrinolytic protein comprised of the polypeptide having the following amino acid sequence (SEQ ID NO:1):

```
Ala Gln Ser Val Pro Tyr Gly Ile Ser Gln Ile Lys Ala Pro Ala
 1               5                  10                   15
Leu His Ser Gln Gly Tyr Thr Gly Ser Asn Val Lys Val Ala Val
                20                  25                   30
Ile Asp Ser Gly Ile Asp Ser Ser His Pro Asp Leu Asn Val Arg
                35                  40                   45
Gly Gly Ala Ser Phe Val Pro Ser Glu Thr Asn Pro Tyr Gly Asp
                50                  55                   60
Gly Ser Ser His Gly Thr His Val Ala Gly Thr Ile Ala Ala Leu
                65                  70                   75
Asn Asn Ser Ile Gly Val Leu Gly Val Ala Pro Ser Ala Ser Leu
                80                  85                   90
Tyr Ala Val Lys Val Leu Asp Ser Thr Gly Ser Gly Gln Tyr Ser
                95                 100                  105
Trp Ile Ile Asn Gly Ile Glu Trp Ala Ile Ser Asn Asn Met Asp
               110                 115                  120
Val Ile Asn Met Ser Leu Gly Gly Pro Thr Gly Ser Thr Ala Leu
               125                 130                  135
Lys Thr Val Val Asp Lys Ala Val Ser Ser Gly Ile Val Val Ala
               140                 145                  150
Ala Ala Ala Gly Asn Glu Gly Ser Ser Gly Ser Thr Ser Thr Val
               155                 160                  165
Gly Tyr Pro Ala Lys Tyr Pro Ser Thr Ile Ala Val Gly Ala Val
               170                 175                  180
Asn Ser Ser Asn Gly Arg Ala Ser Phe Ser Ser Val Gly Ser Glu
               185                 190                  195
Leu Asp Val Met Ala Pro Gly Val Ser Ile Gln Ser Thr Leu Pro
               200                 205                  210
Gly Gly Thr Tyr Gly Ala Tyr Asn Gly Thr Ser Met Ala Thr Pro
               215                 220                  225
His Val Ala Gly Ala Ala Ala Leu Ile Leu Ser Lys His Pro Thr
               230                 235                  240
Trp Thr Asn Ala Gln Val Arg Asp Arg Leu Glu Ser Thr Ala Thr
               245                 250                  255
Tyr Leu Gly Asn Ser Phe Tyr Tyr Gly Lys Gly Leu Ile Asn Val
               260                 265                  270
Gln Ala Ala Ala Gln
               275
``` said method consisting sequentially the steps of:

(1) adding an alcohol or ammonium sulfate to an aqueous extract of Natto or *Bacillus natto* to precipitate a crude fraction, (2) applying the crude fraction on a hydrophobic carrier equilibrated with a neutral or weakly basic buffer to adsorb the fraction onto a column and eluting the absorbed fraction with water or neutral or weakly basic buffer from the column, (3) passing the eluate through an anion exchanger equilibrated with a neutral or weakly basic buffer to adsorb the impurities onto the exchanger and obtaining a purified fraction as the effluent, or applying the eluate on a cation exchanger equilibrated with a neutral or weakly basic buffer to adsorb the fraction onto the exchanger and eluting a purified fraction with a neutral or weakly basic buffer containing a salt, (4) applying the purified fraction on a gel filtration carrier equilibrated with a neutral or weakly basic buffer containing a salt, and (5) recovering a purified fibrinolytic protein.

2. The biologically pure fibrinolytic protein prepared by the method of claim 1.

3. A fibrinolytic composition which comprises the protein of claim 2 and a pharmaceutically acceptable carrier.

4. A thrombolytic composition for oral administration which comprises the protein of claim 2 and a pharmaceutically acceptable carrier.

* * * * *

UNITED STATES PATENT AND TRADEMARK OFFICE
CERTIFICATE OF CORRECTION

PATENT NO. : 5,750,650
DATED : May 12, 1998
INVENTOR(S) : Koichiro Nakanishi, et al It is certified that error appears in the above-indentified patent and that said Letters Patent is hereby corrected as shown below:

On title page between items [76] and [21] insert:

--[73] Assignee: JCR Pharmaceuticals Co., Ltd., Hyogo, Japan--

Signed and Sealed this

Seventeenth Day of November, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:2:

( i ) SEQUENCE CHARACTERISTICS:
( A ) LENGTH: 4
( B ) TYPE: AMINO ACID
( C ) STRANDEDNESS: Unknown
( D ) TOPOLOGY: Unknown ( i i ) SEQUENCE DESCRIPTION: SEQ ID NO:2:

Ala Ala Pro Phe